United States Patent [19]

Quadbeck-Seeger et al.

[11] 4,032,571
[45] June 28, 1977

[54] MANUFACTURE OF 2-AMINO-3,5-DINITROBENZAMIDE

[75] Inventors: Hans-Juergen Quadbeck-Seeger, Bad Duerkheim; Dieter Schneider, Edingen, both of Germany

[73] Assignee: BASF Aktiengesellschaft, Ludwigshafen (Rhine), Germany

[22] Filed: Apr. 18, 1975

[21] Appl. No.: 569,270

[30] Foreign Application Priority Data

May 8, 1974 Germany ............................ 2422239

[52] U.S. Cl. .............................. 260/558 A; 260/688
[51] Int. Cl.$^2$ ........................................ C07C 102/02
[58] Field of Search ........... 260/558 A, 244 A, 688

[56] References Cited

UNITED STATES PATENTS

| | | | |
|---|---|---|---|
| 1,283,617 | 11/1918 | Andrews | 260/688 X |
| 1,887,820 | 11/1932 | Ossenbeck et al. | 260/244 A |
| 2,370,558 | 2/1945 | Mares | 260/688 X |
| 2,826,611 | 3/1958 | Fischback et al. | 260/688 X |
| 3,090,789 | 5/1963 | Dehn, Jr. et al. | 260/688 X |
| 3,100,797 | 8/1963 | Harris et al. | 260/688 X |
| 3,631,060 | 12/1971 | Sklarz et al. | 260/688 X |

OTHER PUBLICATIONS

Staiger et al. "Isatoic Anhydride II Reactions of Isatoic Anhydride with Ammonia" in J. Org. Chem. 13,347 (1948), pp. 347–352.

Staiger et al. "Isatoic Anhydride III Reactions with Primary and Secondary Amines" pp. 1427–1439 (1953).

*Primary Examiner*—Allen B. Curtis
*Attorney, Agent, or Firm*—Keil, Thompson & Shurtleff

[57] ABSTRACT

2-Amino-3,5-dinitrobenzamide is manufactured by nitration of isatoic anhydride with a nitrating mixture of a particular composition at from −20 to +80° C, followed by reaction of the resulting acid phase with ammonia. The product is a starting material for the manufacture of dyes and pesticides.

4 Claims, No Drawings

MANUFACTURE OF 2-AMINO-3,5-DINITROBENZAMIDE

The invention relates to a new process for the manufacture of 2-amino-3,5-dinitrobenzamide by nitration of isatoic anhydride with a nitrating mixture of a particular composition at from −20 to +80° C, followed by reaction of the resulting acid phase with ammonia.

The nitration of o-chlorobenzoic acid, obtainable from o-chlorotoluene, to 3,5-dinitro-2chlorobenzoic acid is known from Rec. Trav. Chim. Pays-Bas 53, 988 − 1000 (1934). Reaction of this product with phosphorus pentachloride gives the corresponding acid chloride which reacts with concentrated ammonia at elevated temperatures, giving 2-amino-3,5-dinitrobenzamide. Thus this end product can only be manufactured by an involved and uneconomical method entailing several reaction stages. The process is unsatisfactory, particularly on an industrial scale, with regard to the yield and purity of the end product and with regard to simplicity, economy and ease of control in operation.

The object of the present invention is to provide a simpler and more economical process for making 2-amino-3,5-dinitrobenzamide in better yield and higher purity.

We have found that 2-amino-3,5-dinitrobenzamide may be obtained by an advantageous method wherein, in a first step, isatoic anhydride is nitrated with nitric acid and oleum in a ratio of 0.5 to 20 moles of sulfur trioxide per mole of nitric acid, in the presence of organic solvents, at from −20 to +80° C, whilst in a second step the acid phase, formed during nitration, of the two-phase reaction mixture is reacted with ammonia.

The reaction can be represented by the following equations:

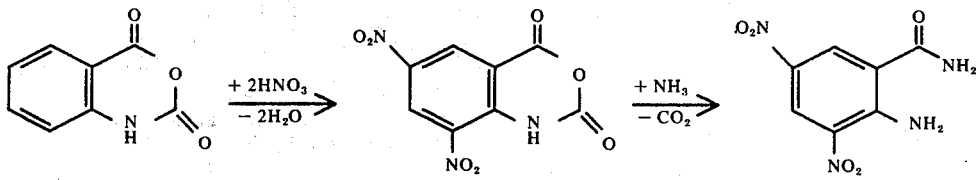

Compared to the conventional process, the process of the invention surprisingly produces 2-amino-3,5-dinitrobenzamide more simply and more economically, and in better yield and higher purity. The end product is obtained by a one-pot method entailing 2 steps, without working up the nitration reaction mixture and isolating the dinitroisatoic anhydride formed. As a result of the reaction being carried out in a two-phase system and only requiring small amounts of sulfuric acid, working up of the mixture is simple and dinitroisatoic anhydride which hydrolyzes readily, is not hydrolyzed by the water formed during the reaction. Furthermore, the salt content of the effluent is low compared to that from conventional nitration conditions so that the process improves the effluent situation.

The nitration is carried out with nitric acid preferably concentrated or fuming nitric acid, in the presence of oleum, i.e. sulfuric acid containing free $SO_3$. In general, nitric acid of from 85 to 100, preferably from 95 to 100, per cent strength by weight, and oleum containing from 5 to 90, preferably from 60 to 70, per cent by weight of $SO_3$ are used. The mixture of nitric acid and oleum, i.e. the nitrating acid, should contain from 0.5 to 20, preferably from 0.8 to 1.12, moles of $SO_3$ per mole of nitric acid. As a rule, from 2 to 5 moles, preferably from 2 to 2.5 moles, of nitric acid per mole of starting material are used. Instead of nitric acid, the reaction mixture may contain compounds which form this acid, e.g. inorganic nitrates, such as sodium nitrate or potassium nitrate, in appropriate amounts. Where appropriate, urea is employed as a nitration catalyst, suitably in amounts of from 10 to 100, preferably from 45 to 55, % by weight, based on isatoic anhydride.

The reaction is carried out at from −20° to +80° C, in the first step preferably at from 0° C to 50° C, especially from 20° to 30° C, and in the second step preferably at from 25° to 60° C, at atmospheric or superatmospheric pressure, batchwise or continuously. In the first step, the reaction is carried out in the presence of organic solvents which are inert under the reaction conditions; in the second step, water, in the form of the aqueous ammonia solution, is generally used. Suitable organic solvents are, e.g., halohydrocarbons, especially chlorohydrocarbons, for example tetrachloroethylene, amyl chloride, cyclohexyl chloride, dichloropropane, methylene chloride, dichlorobutane, isopropyl bromide, n-propyl bromide, butyl bromide, chloroform, chloronaphthalene, dichloronaphthalene, carbon tetrachloride, tetrachloroethane, trichloroethane, trichloroethylene, pentachloroethane, o-, m- and p-difluorobenzene, 1,2-dichloroethane, 1,1-dichloroethane, n-propyl chloride, 1,2-cis-dichloroethylene, n-butyl chloride, 2-, 3-and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane, aliphatic or cycloaliphatic hydrocarbons, e.g. heptane, nonane, pinane, gasoline fractions of boiling range from 70 to 190° C, cyclohexane, methylcyclohexane, petroleum ether, decalin, hexane, ligroin, 2,2,4-trimethylpentane, 2,2,3-trimethylpentane, 2,3,3-trimethylpentane and octane, and appropriate mixtures. Suitably, the solvent is used in amounts of from 400 to 10,000% by weight, preferably from 700 to 1,000% by weight, based on starting material.

The ammonia used in the second reaction step is suitably in the form of an aqueous solution of from 20 to 30 per cent strength by weight. As a rule, from 9 to 25, preferably from 12 to 15, moles of ammonia are emplyed per mole of isatoic anhydride. The pH of the acid phase is preferably adjusted to from 8 to 10 by addition of ammonia in the second reaction step.

The reaction may be carried out as follows: a mixture of starting material, nitrating acid and organic solvent is kept at the reaction temperature for from 2 to 4 hours. The starting mixture is advantageously prepared by slowly adding the nitrating acid to the mixture of the other two components, e.g. over the course of from 0.5 to 1.5 hours. After completion of the first step of the reaction according to the invention, the two phases of the reaction mixture separate surprisingly rapidly. At that stage it is possible to add the ammonia solution directly to the lower phase which contains the sulfuric acid and which is optionally diluted with ice, then to separate off the upper, organic phase and to isolate the end product in the usual manner, for example by filtration, from the phase which is now ammoniacal. However, it is more expedient first to separate from one another the phases of the reaction mixture from the first step, then to add the phase containing the sulfuric acid to the ammonia solution, and to isolate the end product in the above manner.

2-Amino-3,5-dinitrobenzamide which may be manufactured in accordance with the process of the invention is a valuable starting material for the manufacture of dyes and pesticides. Thus, it is possible to convert it, by elimination of water, into 3,5-dinitro-2-amino-benzonitrile, which is a valuable diazo component for the manufacture of blue azo dyes (compare, e.g., German Published Applications 1,644,141, 2,028,395, 1,905,364 and 1,928,372).

The parts mentioned in the Examples which follow are by weight.

EXAMPLE 1 a. Nitrating acid 143 parts of 98 per cent strength by weight nitric acid are added to 277 parts of oleum containing 65 per cent by weight of $SO_3$, whilst keeping the temperature at from 30° to 50° C by cooling with ice. The addition is made in the course of 45 minutes.

b. Nitration and reaction with ammonia 163 parts of isatoic anhydride are introduced into 1,250 parts of 1,2-dichloroethane. The nitrating acid prepared according to 1 (a) is added in the course of 45 minutes, whilst stirring thoroughly and keeping the temperature at from 20° to 25° C by cooling with ice. The mixture is then stirred for 3 hours, during which an emulsion forms. After completion of the reaction, the sulfuric acid phase is allowed to separate out below the organic phase for 30 minutes. The sulfuric acid phase is then added to 860 parts of 25 percent strength by weight ammonia solution in the course of 30 minutes, and the temperature is kept at from 25° to 50° C by gradual addition of 800 parts of ice. Stirring is continued for 30 minutes, the mixture is then cooled to 25° C and the product is filtered off. After washing the filter residue with 200 parts of water and drying (at 60° C in vacuo), 200 parts, corresponding to 88% of theory, of 2-amino-3,5-dinitrobenzamide melting, with decomposition, at 278° C are obtained.

EXAMPLE 2

The reaction is carried out analogously to Example 1 with 1,600 parts of 1,1,2,2-tetrachloroethane. 198 parts of 2-amino-3,5-dinitrobenzamide (corresponding to 87% of theory) melting at 278° C are obtained.

EXAMPLE 3

The reaction is carried out analogously to Example 1, with 1.600 parts of carbon tetrachloride. 200 parts of 2-amino-3,5-dinitrobenzamide (corresponding to 88% of theory) melting at 278° C are obtained.

We claim:

1. A process for the manufacture of 2-amino-3,5-dinitrobenzamide which comprises nitrating at −20° C to 80° C isatoic anhydride dissolved in an inert organic solvent with an acid mixture consisting of 85–100% strength nitric acid and oleum, said acid mixture containing 0.5 to 20 moles of sulfur trioxide per mole of nitric acid, to produce 3,5-dinitroisatoic anhydride, allowing the reaction mixture to separate into an organic phase and an acid phase containing the 3,5-dinitroisatoic anhydride, adding 20–30% strength aqueous ammonia to the resultant acid phase in an amount of 9 to 25 moles of ammonia per mol of isatoic anhydride, and reacting the ammonia and the acid phase to produce a high yield of 2-amino-3,5-dinitrobenzamide.

2. A process as claimed in claim 1 wherein the amount of said organic solvent is 400 to 10,000% by weight, based on said isatoic anhydride.

3. A process as claimed in claim 1 wherein the nitration is carried out at 0°–50° C and the ammonia-acid phase reaction is carried out at 25°–60° C, using 20–30% strength aqueous ammonia.

4. A process as claimed in claim 1 wherein the amount of ammonia added raises the pH of the separated acid phase to 8–10.

* * * * *